United States Patent [19]

Georgi et al.

[11] 4,338,932
[45] Jul. 13, 1982

[54] METHOD AND APPARATUS FOR FLUID FLOW CONTROL

[75] Inventors: Heinz W. Georgi; Wallace L. Knute, both of Del Mar; Richard L. Foreman, Lemon Grove, all of Calif.

[73] Assignee: IVAC Corporation, San Diego, Calif.

[21] Appl. No.: 204,768

[22] Filed: Nov. 7, 1980

[51] Int. Cl.³ ............................................. A61M 5/00
[52] U.S. Cl. .................................................. 128/214 E
[58] Field of Search ...................... 128/214 E; 222/76; 137/487.5

[56] References Cited

U.S. PATENT DOCUMENTS

| | | | |
|---|---|---|---|
| 4,037,598 | 7/1977 | Georgi | 128/214 E |
| 4,048,474 | 9/1977 | Oleson | 128/214 E |
| 4,077,405 | 3/1978 | Haerten et al. | 128/214 E |
| 4,191,184 | 3/1980 | Carlisle | 128/214 E |

*Primary Examiner*—William E. Kamm
*Attorney, Agent, or Firm*—Fulwider, Patton, Rieber, Lee & Utecht

[57] ABSTRACT

An improved method and apparatus for parenteral administration of medical fluids, wherein a normally shut-off intravenous feeding tube is selectively opened at a frequency and open period duration automatically regulated by a digital control system to establish a fluid flow rate at any selected rate over a wide dynamic range. Measured and desired flow rates are converted to digital electrical signals and compared, the electrical difference being used to vary a control voltage which establishes the width of energizing pulses controlling a member for opening the feeding tube. The frequency of the energizing pulses is preferably a non-integral multiple of the desired drop flow rate and varies from a very high ratio, e.g. 15.5, at very low flow rates to a much smaller ratio, e.g. 2.5, at very high flow rates.

30 Claims, 4 Drawing Figures

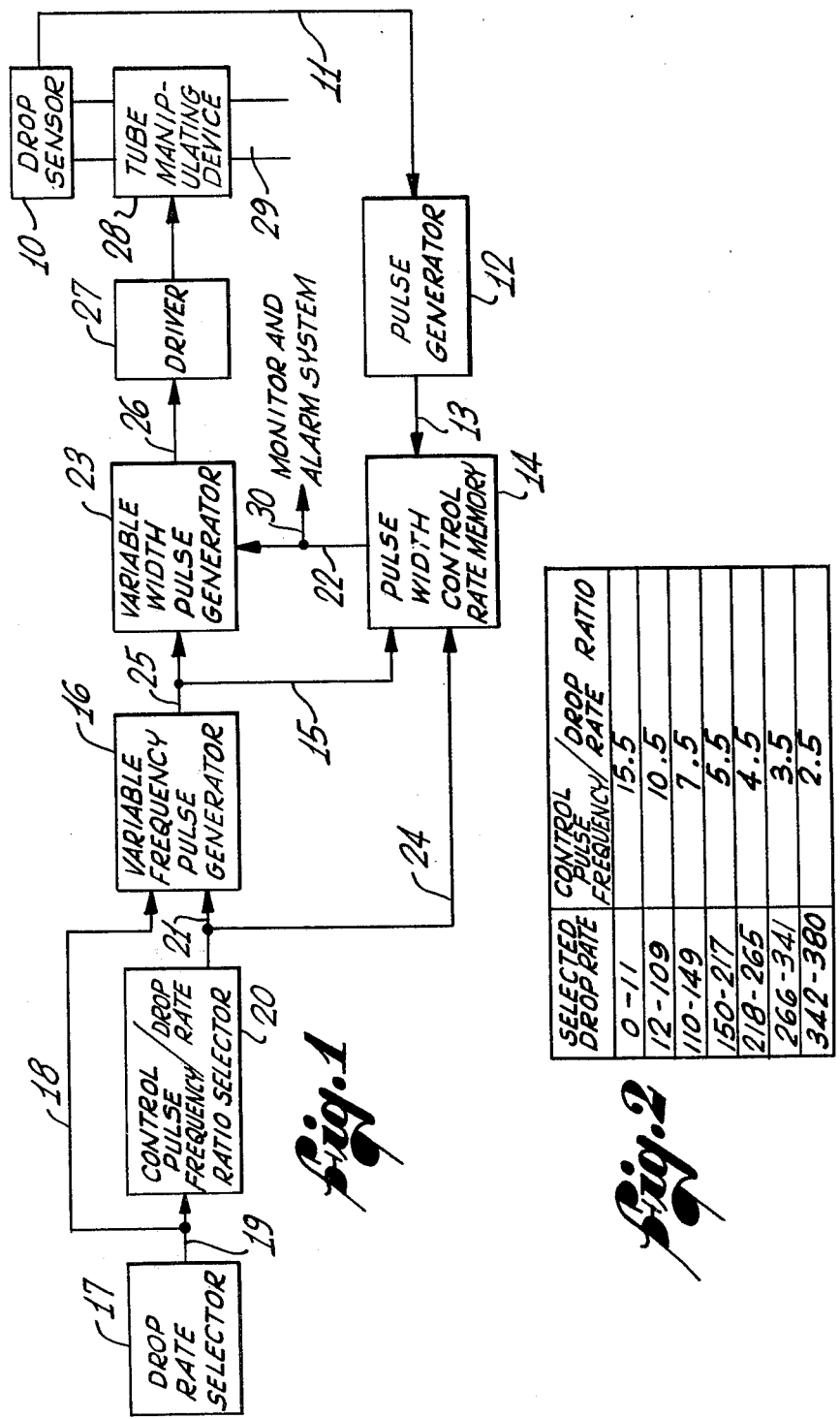

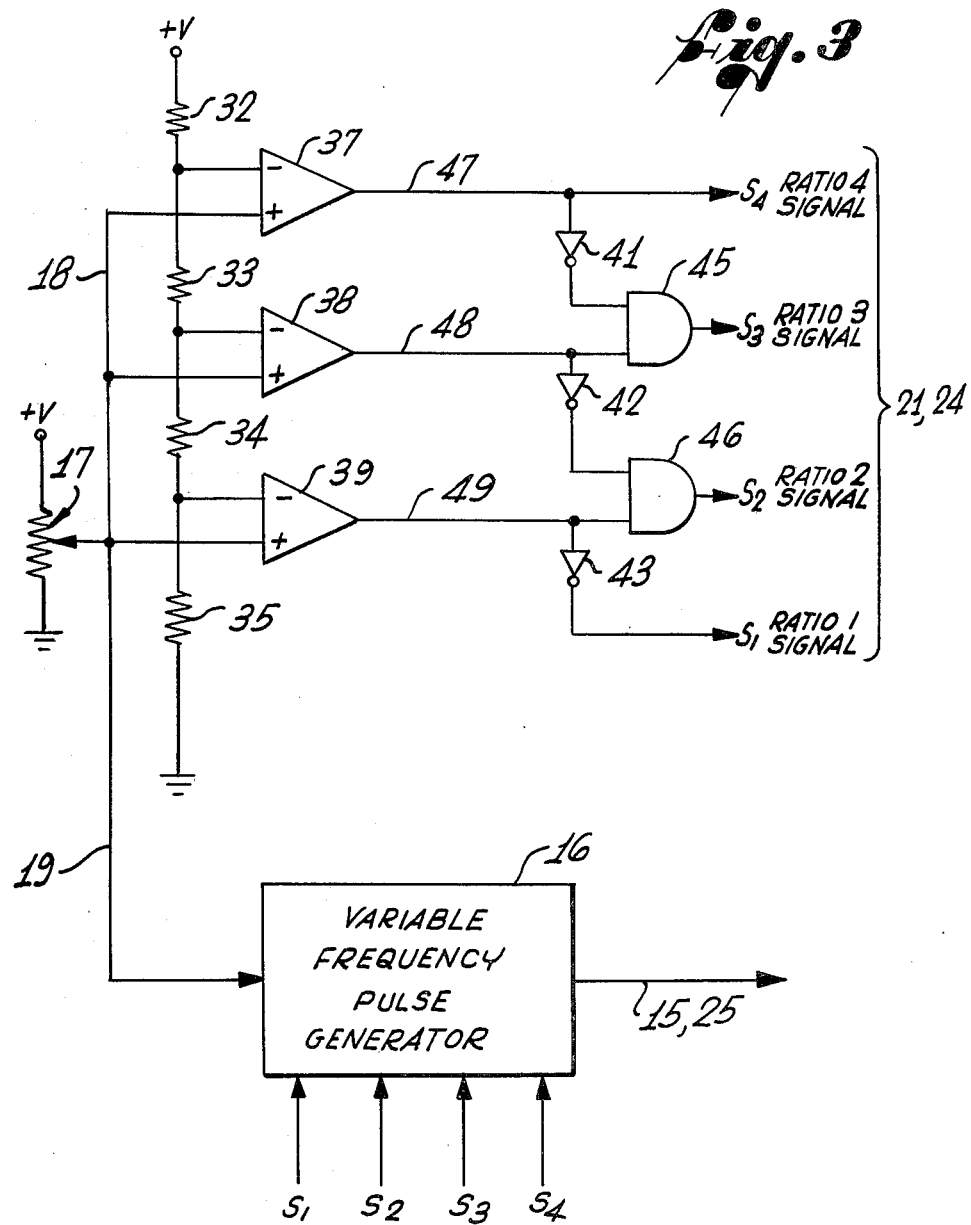

METHOD AND APPARATUS FOR FLUID FLOW CONTROL

BACKGROUND OF THE INVENTION

This invention relates generally to improvements in fluid flow control systems and, more particularly, to a new and improved automatic, self-regulating, highly accurate drop flow control system for parenteral administration (referred to herein as "intravenous administration" or "IV administration") of medical fluids over a wide range of fluid flow rates. More specifically, the invention relates to improvements in IV controllers using electrically actuated IV tube pinchers.

The usual medical procedure for the gradual IV administration of fluids into the human body, such as fluid replacement, liquid nutrients, blood or plasma, makes use of apparatus which is commonly referred to in the medical art as an intravenous solution administration set. The set typically is a disposable plastic product, and comprises a drop chamber adapted to be connected to a fluid source, a length of tubing extending from the chamber to the patient and a valve mechanism, such as a roller clamp on the tubing.

The drip chamber serves the dual function of allowing a nurse or other attendant to observe the rate at which the fluid drips out of the fluid source and also creates a reservoir for the fluid at the lower end of the drip chamber to insure that no air enters the main feeding tube leading to the patient.

While observation of the rate of drop flow via the drip chamber is a simple way of controlling the amount of fluid fed to a patient over a period of time, its ultimate effectiveness requires that a relatively constant vigil be maintained on the drop flow, lest it cease entirely due to exhaustion of the fluid supply or vary unacceptably from the set rate.

By way of example, it has been a common practice in hospitals to have nurse periodically monitor drop flow rate at each intravenous feeding or parenteral infusion station. Such monitoring of drop flow is a tedious and time consuming process, resulting in a substantial reduction of the available time of qualified medical personnel for other important duties. Typically, the nurse monitoring drop flow rate will use a watch to time the number of drops flowing in an interval of one or more minutes, and she will then mentally perform the mathematics necessary to convert the observed data to an appropriate fluid flow rate, e.g., in milliliters per hour or drops per minute. If the calculated flow rate is substantially different than the prescribed rate, the nurse must manually adjust the roller clamp for a new rate, count drops again, and recalculate to measure the new rate.

Obviously, each of the aforedescribed measurements and calculations and flow rate adjustments usually take several minutes time which, when multiplied by the number of stations being monitored and the number of times each station should be monitored per day, can result in a substantial percentage of total personnel time available.

In addition to the aforedescribed difficulties, the IV administration of medical fluids by gravity induced hydrostatic pressure infusion of the liquid from a fluid source suspended above a patient, is susceptible to fluid flow rate variation due to changes in the fluid level in the bottle, changes in temperature, changes in the venous or arterial pressure of the patient, patient movement, and drift in the effective setting of the roller clamp or other valve mechanism pinching the feeding tube. Moreover, there are a number of situations, such as in intensive care, cardiac and pediatric patients, or where rather critical drugs are being administered, where the desired drop flow rate must be capable of precise selection and must not drift beyond certain prescribed limits.

It will be apparent, therefore, that some of the most critical problems confronting hospital personnel faced with a heavy duty schedule and limited time availability are the problems of quickly, easily, reliably and accurately monitoring and regulating drop flow rate in the IV administration of medical fluids.

In recent years, a number of electrical monitoring systems, drop flow controllers and infusion pumps have been developed to accomplish the various tasks of sensing and regulating drop flow rates. However, while such monitoring and drop rate control devices have generally served their purpose, there is a continuing need for improvement in accuracy and precision of adjustment over a wide range of selected flow rates. Difficulties have been experienced in connection with establishing and maintaining such accurate drop flow rates at the extreme ends of the operating range, i.e., at very high flow rates and very low flow rates. Such difficulties are manifested in IV controllers by sticking of the IV tube as it opens and closes at low drop flow rates and failure of the IV tube pincher to completely close off the IV tube at high drop flow rates because the mechanical inertia of the plunger may be too high to respond to each electrical pulse in a very high frequency pulse train.

Hence, those concerned with the development and use of IV fluid administration systems, and particularly those concerned with the design of automatic fluid flow control systems, such as IV controllers, have recognized the need for improved, relatively simple, economical, reliable, stable and accurate devices for fluid flow control which obviate the aforedescribed difficulties. The present invention clearly fulfills this need.

SUMMARY OF THE INVENTION

Briefly, and in general terms, the present invention provides a new and improved method and apparatus for controlling drop flow in the IV administration of medical fluids, wherein the frequency and width of control pulses which open a normally shut-off feeding tube are controlled by a digital system capable of sensing and regulating drop flow rate accurately over a wide range of flow rates. More particularly, the present invention provides novel improvements in drop flow controllers of the type described in U.S. Pat. No. 3,800,794, issued Apr. 4, 1974, for Methods and Apparatus for Fluid Flow Control, inventor Heinz W. Georgi, and the disclosure of the latter patent is specifically incorporated herein by reference. The improvement of the present invention provides for varying the ratio of the control pulse frequency to the drop flow rate as a function of the selected drop flow rate.

In the system of the present invention, as well as in the system of the aforementioned U.S. Pat. No. 3,800,794, the system for establishing control pulse frequency is an open loop subsystem wherein the control pulse frequency representing desired flow rate is a relatively high, preferably non-integral, multiple of the actual drop flow rate frequency (typically expressed as DPM, or drops per minute) which results in less drop distortion and more consistently repeatable drop size from one drop to another.

Additional control over drop flow rate is accomplished by varying control pulse width, i.e., the open period duration for the feeding tube for each control pulse. Variation of control pulse width to regulate actual drop flow rate so that it is maintained within close tolerances at the desired flow rate is established by a closed loop subsystem.

By way of example, a feeding tube clamping member (normally in the tube shut-off position) is repeatedly moved to the tube-open position by a driver which is, in turn, energized by pulses from a variable pulse generator which produces control pulses at a frequency which is a high multiple of the desired drop flow rate. The width of each control pulse is determined by the amplitude of a control voltage produced by a rate memory which compares a pair of electrical signals proportional to the measured and desired drop flow rates, respectively, and integrates the electrical difference between these signals with the proper polarity to either increase or diminish the amplitude of the control voltage. In this way, precise regulation of the control pulses to the proper pulse width for establishing the desired drop flow rate is accomplished.

The present invention provides further novel improvements in the aforedescribed system by varying the ratio of the control pulse frequency to drop flow rate frequency so that the ratio is higher at low drop flow rates and lower at high drop flow rates. This variable ratio accommodation mitigates problems of IV tube wall sticking, at very low flow rates, and tube pincher hover or inertial lag at very high drop flow rates. Typically, and by way of example in a presently preferred embodiment of the invention, the ratio may be increased to 15½ at very low drop flow rates, such as 11 DPM or less, and decreased to 2½ at very high drop flow rates, such as 342 DPM or more. Drop flow rates between these limits are matched to a plurality of different ratios between 15½ and 2½. The values of control pulse to drop rate ratio may be varied continuously, or as a step-function, and may be accomplished by any analog or digital means, including microprocessors, known to those skilled in the art, without departing from the spirit of the invention.

The new and improved fluid flow control system of the present invention is extremely accurate, reliable and easy to use in selecting and maintaining drop flow rates throughout a wide range. Hence, the system of the present invention further minimizes the time consuming and error prone aspects of human monitoring and flow rate adjustment and frees medical personnel for other duties.

These and other objects and advantages of the invention will become apparent from the following more detailed description, when taken in conjunction with the accompanying drawings of illustrative embodiments.

BRIEF DESCRIPTION OF THE DRAWINGS

FIG. 1 is a block diagram of a fluid flow control system in accordance with the present invention;

FIG. 2 is a table of typical values of control pulse frequency to drop rate ratio for selected drop rates, in accordance with a presently preferred embodiment of the invention;

FIG. 3 is a combined electrical schematic and block diagram of a drop rate selection and control pulse generation subsystem, including means for generating corresponding appropriate ratios of control pulse frequency to desired drop rate, suitable for use in the flow control system of the present invention.

DESCRIPTION OF THE PREFERRED EMBODIMENT

Figure 4:
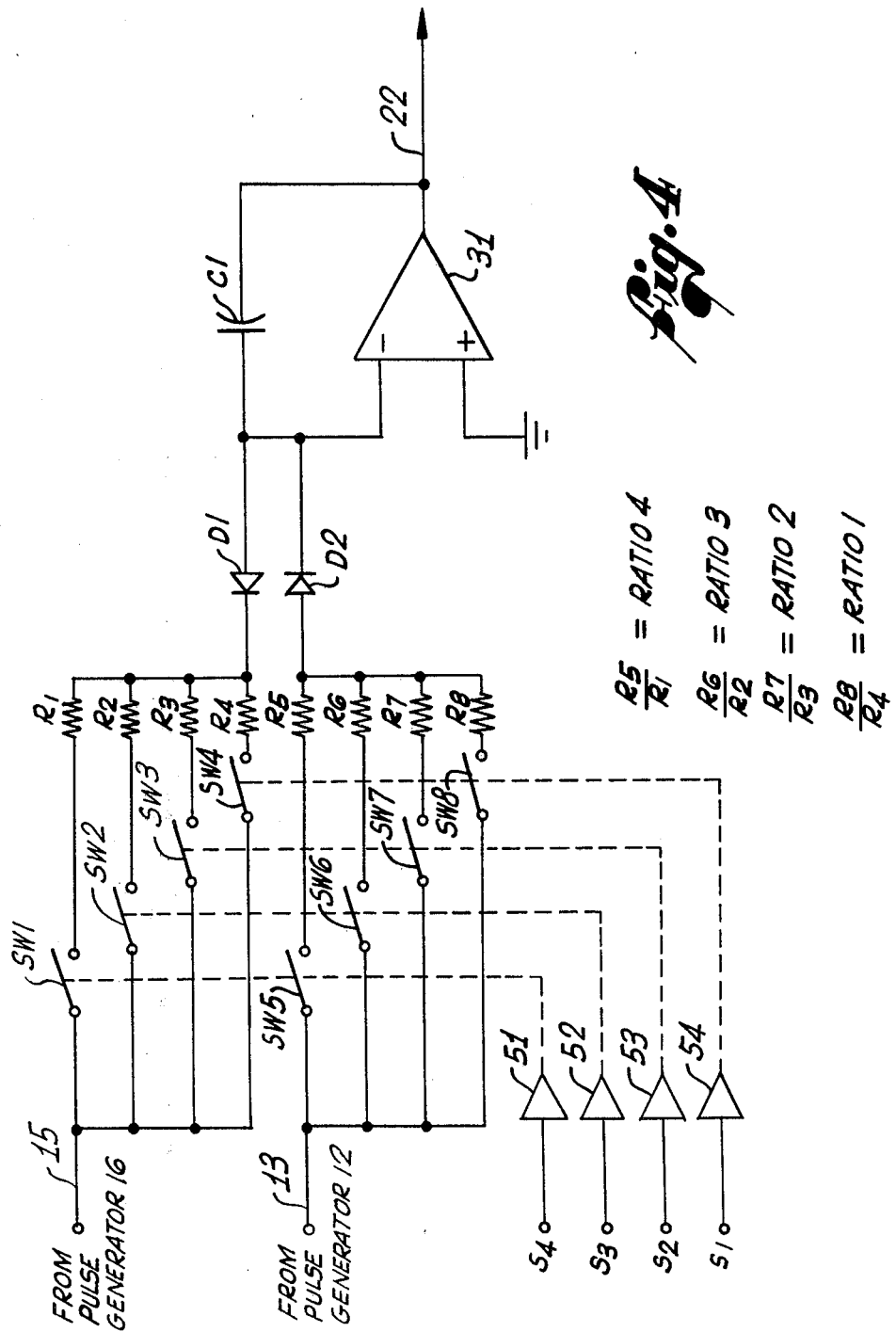
FIG. 4 is an electrical schematic diagram of a rate memory subsystem operating under the control of the variable control pulse frequency to desired drop rate ratios generated by the subsystem shown in FIG. 3.

Referring now particularly to FIG. 1 of the drawings, there is shown a drop flow control system embodying the novel features of the present invention. In the ensuing description, while reference will be made to the term "IV" normally connoting intravenous administration or even more broadly, parenteral administration, it is to be understood that this is by way of example only, and the flow control system of the present invention is suitable for other medical fluid administration.

In order to control drop flow rate, it is necessary to continuously monitor the actual drop flow as it occurs in an IV solution administration set. This is accomplished in the system of FIG. 1 by a drop flow monitor which includes a drop sensor 10 and a pulse generator 12 adapted to detect each drop as it falls and generate an electrical pulse train at a frequency directly proportional to the drop rate.

The drop sensor 10 monitors drop flow in a drip chamber (not shown) of the IV administration set and typically may include a sensor housing (not shown) containing a reference light source spaced from a photocell to define an optical sensing gap therebetween, with a reference light beam normally impinging upon the photocell. The housing is appropriately clamped upon the drip chamber of the IV set with the drip chamber positioned within the sensing gap to intercept the reference beam. A falling drop of fluid within the drip chamber interrupts the reference beam, and the variation in the electrical response of the photocell is communicated to appropriate circuitry indicating the presence of a drop. While a photocell monitoring device is ideally suited for the drop sensor 10, it will be appreciated that any drop sensing device capable of providing an electrical indication of the presence of a drop may be used without departing from the spirit and scope of the invention.

The pulse generator 12 receives electrical output from the sensor 10 over line 11 and is typically a conventional Eccles-Jordan monostable flip-flop (one-shot) which provides an output pulse with a prescribed pulse width and amplitude each time a drop is detected by the drop sensor 10. The pulse generator 12 typically provides a positive going pulse train proportional to measured drop flow rate, as an electrical input over line 13 to a pulse-width control rate memory 14.

A second electrical input to the rate memory 14 is provided over line 15 in the form of a negative going pulse train from a variable frequency pulse generator 16. The pulse generator 16 is typically a variable frequency square wave generator which generates a negative pulse train at a frequency determined by a drop rate selection and control pulse frequency to drop rate ratio generation subsystem, such as that shown in more detail in FIG. 3 of the drawings. In this regard, a drop rate selector 17 in FIG. 1 directs its voltage output over line 18 to the variable frequency pulse generator 16 to establish the output pulse frequency from the latter generator and, at the same time, conditions over line 19 a control pulse frequency to drop rate ratio selector 20 which, in turn, determines the appropriate ratio for the selected drop rate and conditions the pulse generator 16 by electrical input over line 21.

The positive pulse train over line 13 from the pulse generator 12, indicative of measured drop flow rate, and the negative pulse train over line 15 from the pulse generator 16, indicative of desired drop flow rate, are combined and compared in the rate memory 14, the electrical difference between the signals indicating measured and desired rates being integrated in the rate memory with the proper polarity to either increase or diminish the amplitude of a d.c. output control voltage which is fed from the memory, over line 22, as an electrical control input to a pulse generator 23 having a selectively variable output pulse width. The variable pulse width generator 23 also receives a pulse train input over line 25 from the variable frequency pulse generator 16. It will be apparent that any variable width pulse generating circuit susceptible to control by the control voltage from the rate memory 14 may be utilized for the variable pulse width generator 23 without in any way departing from the spirit and scope of the present invention.

The pulse width control rate memory 14 also receives an electrical input, over line 24, from the ratio selector 20 so that the pulse trains over lines 13 and 15 are properly weighted. A suitable rate memory subsystem for this purpose is illustrated in FIG. 4 of the drawings.

The output pulses from the pulse generator 23 are directed over line 26 as energizing pulse input to a driver 27 which, in turn, moves a tube manipulating device, such as a clamping member 28, away from a flexible IV feeding tube 29 to thereby open the feeding tube for fluid flow. The clamping member 28 is normally spring-biased to a position which pinches the tube 29 in a shut-off state.

Each output pulse over line 26 causes the clamping member 28 to be retracted and thereby open the feeding tube 29 for the duration of the energizing pulse width.

In accordance with the teachings of the aforementioned U.S. Pat. No. 3,800,794, the control pulse output from the pulse generator 16 directed over lines 15 and 25 is a multiple of the actual drop flow rate frequency desired. As the ratio of driver pulse frequency to actual drop flow rate frequency increases, drop size distortion, and consequent lack of consistent drop size repeatability, diminishes. Best results are achieved with a relatively high, non-integral ratio of driver pulse frequency to desired drop frequency.

It has been discovered that, particularly at very low drop flow rates, the walls of the IV tube 29 display a tendency to stick together and, the longer the period of tube close-off by the clamping member 28, the more pronounced the tube sticking, with its inherent potential for introducing drop flow inaccuracy. This is particularly true for the vinyl IV tubing commonly in use in the parenteral administration of liquids, but is also the case, in varying degrees, for other plastic and elastomer IV tubing materials as well.

It has also been determined that, at higher drop flow rates, the clamping member 28 behaves as a mechanical low pass filter for the driver pulses and can thereby introduce inertial lag so that the clamping member hovers in a partially open position without completely clamping off the IV tube 29 between driver pulses, a condition which also may introduce drop flow inaccuracy.

Hence, in accordance with the invention the ratio of control pulses to drops is varied with selected drop flow rate, rather than being maintained at a constant ratio for all selected drop flow rates. In this connection, the ratio of the control pulse frequency to drop flow rate is varied so that the ratio is higher at low drop flow rates and lower at high drop flow rates. This variable ratio accommodation as a function of selected drop flow rate mitigates problems of IV tube wall sticking, at very low flow rates, and tube pincher hover or inertial lag at very high drop flow rates. Typically, and by way of example in a presently preferred embodiment of the invention, the ratio may be increased to $15\frac{1}{2}$ at very low drop flow rates, such as 11 DPM or less, and decreased to $2\frac{1}{2}$ at very high drop flow rates, such as 342 DPM or more. Drop flow rates between these limits would be selected as a function of selected drop flow rate with appropriate ratio values falling between $15\frac{1}{2}$ and $2\frac{1}{2}$.

FIG. 2 of the drawings is a table of typical values of control pulse frequency to drop rate ratios for selected drop flow rates between zero and 380 DPM, in accordance with a presently preferred embodiment of the invention. The values of control pulse frequency to drop rate ratio may be varied continuously or as a step-function, and may be accomplished by any known analog or digital means, including microprocessors or other computer implementation, without departing from the spirit and scope of the invention.

Hence, in accordance with the present invention, each drop which flows through the IV feeding tube 29 is made up of a multiplicity of smaller drop portions which are attached to each other to form a contiguous fluid body making up the final drop, which is thus grown in steps under the control of the energizing pulses from the pulse generator 23, and the ratio of the energizing pulse frequency to drop flow rate is varied as a function of the selected drop flow rate. The width or duration of the energizing pulses is varied by the closed loop system including the drop sensor 10, pulse generator 12 and rate memory 14 to ensure regulation of the actual drop flow rate measured to the desired drop flow rate indicated by the pulse output from the pulse generator 16.

The control voltage output from the rate memory 14 is also directed over a line 30 to any appropriate monitor and alarm system (not shown) for detecting any out-of-limit conditions. Such monitor and alarm systems may take any form well known in the art, such as high and low level discriminators for selectively triggering aural or visual alarms (not shown).

One example of a subsystem suitable for performing the functions of the drop rate selector 17, control pulse frequency to drop rate ratio selector 20 and variable frequency pulse generator 16 is shown in FIG. 3 of the drawings.

The system of FIG. 3 provides, by way of example, means for the determination of four different ratio signals S1-S4, corresponding to Ratio 1-Ratio 4 of control pulse frequency to drop rate. However, it is to be understood that the choice of four ratios is illustrative only, and any number of ratios which are an appropriate function of the selected drop rate may be used, and determined in any convenient manner, analog, digital or by computer, without departing from the invention.

The rate selector 17 is schematically depicted in FIG. 3 as a variable potentiometer which provides an analog signal over line 19 as input to the variable frequency pulse generator 16. The rate selector 17 also provides the same electrical output over line 18 to a comparator network for determination of the ratio signals S1-S4.

The comparator network includes four resistors 32-35 connected in series between a positive voltage source and ground as a conventional weighted resistor ladder, three comparators 37-39, three logical inverters 41-43, and a pair of And gates 45, 46. Each comparator receives one input from the resistor ladder and the other input from the rate selector 17. The comparator network determines a single control pulse frequency to drop rate ratio exclusively at any one time, so that only one of the ratio signals S1-S4 will be "true" at any one time, with all of the other ratio signals being "false" at that time.

Assuming, for example, a very high drop rate is selected, then the electrical outputs from all of the comparators 37-39 over lines 47-49, respectively, will all be "true". Hence, the ratio signal S4 on line 47 will be "true". However, in view of the inverters 41-43, all of the ratio signals S1-S3 will be "false". If a lower drop rate is selected, the output over line 47 will be "false", but lines 48 and 49 will still be "true". The "false" output on line 47 will be inverted to a "true" input to the And gate 45, so that ratio signal S3 will be "true". However, all other ratio signals S1, S2 and S4 will still be "false". Similarly, if still lower drop rates are selected, only the output from comparator 39, over line 49, will be "true", which will result in the ratio signal S2 being "true" at the output of the And gate 46. All other ratio signals S1, S3 and S4 will be "false". If still lower drop rates are selected, then none of the signals over lines 47, 48, 49 will be "true" and, therefore, the only "true" ratio signal will be the inverted output from the inverter 43 which is the ratio signal S1. All of the other ratio signals S2-S4 will be "false".

The ratio signals S1-S4 are used to control the variable frequency pulse generator 16 to alter the frequency output of the pulse generator for any given control voltage input over line 19 from the rate selector 17. The ratio signals S1-S4 may modify the pulse generator 16 in any conventional fashion, as by switching component values in an oscillator circuit to alter oscillator frequency.

One embodiment of electrical circuitry suitable for carrying out the necessary functions of the pulse width control rate memory 14 is illustrated in FIG. 4 of the drawings. The negative pulse train from the pulse generator 16 is directed over line 15 through a selected one of a plurality of current determining resistors R1-R4 and diode D1 as input to the negative channel of a conventional operational amplifier 31 which, together with a capacitor C1, is electrically wired in a conventional integrating configuration to provide the d.c. control voltage output over line 22 to the variable width pulse generator 23. In a similar manner, the positive pulse train from the pulse generator 12 is directed over line 13 through a selected one of a plurality of current determining resistors R5-R8 and diode D2 as an additional input to the same negative channel of the amplifier 31 as the negative pulse train passed by the diode D1.

If the measured and desired flow rates are the same, then the net electrical input to the amplifier 31 is zero, since the positive and negative pulses essentially cancel each other out, and the d.c. control voltage output over line 22 stays constant. If the desired rate is higher than the measured rate, the control voltage output drifts more positive while, on the other hand, the control voltage drifts more negative if the flow rate measured is higher than the desired flow rate. It will also be apparent that, in the event the electrical inputs to the amplifier 31 are disconnected, the d.c. control voltage output of the amplifier will hold constant at its last level prior to disconnection.

As shown in FIG. 4, the particular resistors R1-R4 and R5-R8 are selected in corresponding pairs by ganged switches SW1-SW4 and SW5-SW8, respectively, under control of suitable relay drivers 51-54. These relay drivers 51-54 are, in turn, energized selectively by the output ratio signals S1-S4 from the control pulse frequency to drop rate ratio selector subsystem of FIG. 3. The resistive ratios are weighting terms for the pulse trains to the integrator. Of course, the switching subsystem may be accomplished by relays, FET switches, computer control or any equivalent devices.

In this way, as illustrated for example in FIGS. 2 and 3 of the drawings, the variable frequency pulse generator 16 and pulse width control rate memory 14 are properly adjusted and compensated for the variable ratios of control pulse frequency to drop rate which occur as the desired drop rate is changed by adjustment of the drop rate selector 17.

The new and improved method and apparatus for drop flow control, in accordance with the present invention, further satisfies a long existing need in the medical arts for an extremely accurate, relatively low cost, reliable, easy to use system providing digital precision in selecting and maintaining drop flow rates over a very wide range. The system of the present invention functions to maintian selected flow rates substantially independent of changes in temperature, crimps in the feeding tube, variations in venous or arterial pressure of the patient, muscular activity of the patient, or variations in the height of the IV bottle or solution level within the bottle.

It will be apparent from the foregoing that, while particular forms of the invention have been illustrated and described, various modifications can be made without departing from the spirit and scope of the invention. Accordingly, the invention is not to be limited, except as by the appended claims.

We claim:

1. In the parenteral administration of medical fluids by an intravenous set including drop forming means and fluid conduit means coupled to said drop forming means, a method of controlling the rate of drop flow through said fluid conduit means, comprising the steps of:

clamping said fluid conduit to a substantially shut-off state;

repetitively opening and closing said fluid conduit to fluid flow, the frequency of opening said fluid conduit being at a higher frequency than the desired drop flow rate through said fluid conduit, the ratio of said frequency of opening and closing to said desired drop flow rate being higher for relatively low drop flow rates than for relatively high drop flow rates, whereby a plurality of cycles of opening and closing said fluid conduit are required to produce each individual drop of flow.

2. A method as set forth in claim 1, wherein the frequency of opening said tube is an integral multiple of the desired drop flow rate.

3. A method as set forth in claim 1, wherein the frequency of opening said tube is a non-integral multiple of the desired drop flow rate.

4. In the parenteral administration fo medical fluids by an intravenous set including drop forming means and fluid conduit means coupled to said drop forming means, a method of controlling the rate of drop flow through said fluid conduit means, comprising the steps of:
- clamping said fluid conduit to a substantially shut-off state;
- producing control pulses having a frequency higher than a desired drop flow rate through said fluid conduit, the ratio of said control pulses to said desired drop flow rate being higher for relatively low drop flow rates than for relatively high drop flow rates; and
- repetitively opening and closing said fluid conduit to flow in response to said control pulses, the frequency of opening said fluid conduit being at a higher frequency than the desired drop flow rate through said fluid conduit, whereby a plurality of control pulses and cycles of opening and closing said fluid conduit are required to produce each individual drop of flow.

5. A method as set forth in claim 4, wherein said control pulses are produced at a frequency that is a relatively high multiple of the desired drop flow rate.

6. A method as set forth in claim 4, wherein said control pulses are produced at a frequency that is an integral multiple of the desired drop flow rate.

7. A method as set forth in claim 4, wherein said control pulses are produced at a frequency that is a non-integral multiple of the desired drop flow rate.

8. In the parenteral administration of medical fluids by an intravenous set including drop forming means and fluid conduit means coupled to said drop forming means, a method of controlling the rate of drop flow through said conduit means, comprising the steps of:
- clamping said fluid conduit to a substantially shut-off state;
- selecting a desired drop flow rate; and
- repetitively opening and closing said fluid conduit to flow, the frequency at which said conduit is opened being higher than the desired drop flow rate through said fluid conduit, the ratio of said frequency of opening and closing to said desired drop flow rate being higher for relatively low drop flow rates than for relatively high drop flow rates, whereby a plurality of successive cycles of opening and closing said fluid conduit is required to produce each individual drop of flow.

9. A method as set forth in claim 8, wherein said fluid conduit is automatically and continuously opened and closed to provide a continuing drop flow at the desired rate.

10. A method as set forth in claim 8, wherein said frequency is a relatively high multiple of the desired drop flow rate.

11. A method as set forth in claim 8, wherein said frequency is an integral multiple of the desired drop flow rate.

12. A method as set forth in claim 8, wherein said frequency is a non-integral multiple of the desired drop flow rate.

13. A method as set forth in claim 12, wherein said non-integral multiple is varied in the range of approximately $2\frac{1}{2}$ times the desired drop flow rate to $15\frac{1}{2}$ times the desired drop flow rate.

14. In the parenteral administration of medical fluids by an intravenous set including drop forming means and a flexible tube coupled to said drop forming means for carrying drop flow, a method of controlling the rate of drop flow through a flexible tube, comprising the steps of:
- clamping said tube to a substantially shut-off state;
- producing control pulses at a selected frequency greater than the desired rate of drop flow, the ratio of said control pulses to said desired drop flow rate being higher for relatively low drop flow rates than for relatively high drop flow rates;
- monitoring the actual drop flow occurring through said tube;
- selectively varying the duration of each of said control pulses in accordance with the actual drop flow; and repetitively opening and closing said tube to fluid flow in response to said control pulses to regulate the actual drop flow rate so that it conforms to said desired drop flow rate.

15. A method as set forth in claim 14, wherein the frequency of opening said tube is a relatively high multiple of the desired drop flow rate.

16. A method as set forth in claim 14, wherein said multiple is varied in the range of approximately $2\frac{1}{2}$ times the desired drop flow rate to $15\frac{1}{2}$ times the desired drop flow rate.

17. In a system for parenteral administration of liquids by drop flow, apparatus for controlling the rate of drop flow comprising:
- drop forming means;
- a feeding tube coupled to said drop forming means;
- tube clamping means for closing said feeding tube to prevent liquid flow therethrough;
- flow rate setting means for designating a desired flow rate; and
- means responsive to said rate setting means for unclamping said tube at a selected frequency higher than the desired drop flow rate to allow repetitive liquid flow through said feeding tube, the ratio of said frequency of unclamping said tube to said desired drop flow rate being higher for relatively low drop flow rates than for relatively high drop flow rates, whereby a plurality of successive cycles of unclamping said tube are required to produce each individual drop of flow.

18. Apparatus as set forth in claim 17, wherein said means for unclamping said tube operates at a frequency that is a relatively high multiple of the desired drop flow rate.

19. Apparatus as set forth in claim 18, wherein said frequency is an integral multiple of the desired drop flow rate.

20. Apparatus as set forth in claim 18, wherein said frequency is a non-integral multiple of the desired drop flow rate.

21. Apparatus as set forth in claim 20, wherein said non-integral multiple is varied in the range of approximately $2\frac{1}{2}$ times the desired drop flow rate to $15\frac{1}{2}$ times the desired drop flow rate.

22. In a system for parenteral administration of liquids by drop flow through a feeding tube, apparatus comprising:
- clamping means for clamping said feeding tube in a normally shut-off state;

electrical pulsing means for generating control pulses at a rate greater than the desired drop flow rate to periodically energize said clamping means and thereby open said tube to liquid flow, the ratio of the frequency of said control pulses to said desired drop flow rate being higher for relatively low drop flow rates than for relatively high drop flow rates;

rate setting means for generating an electrical signal proportional to desired drop flow rate;

flow monitoring means for monitoring actual drop flow through said tube and generating an electrical signal proportional to measured drop flow rate; and means responsive to both said rate setting means and said flow monitoring means for regulating the pulse length of pulses from said pulsing means.

23. Apparatus as set forth in claim 22, wherein said rate setting means includes a pulse generator for generating said electrical signal as a pulse train at a higher frequency than the desired drop flow rate.

24. Apparatus as set forth in claim 23, wherein said frequency is a relatively high multiple of the desired drop flow rate.

25. Apparatus as set forth in claim 23, wherein said frequency is an integral multiple of the desired drop flow rate.

26. Apparatus as set forth in claim 23, wherein said frequency is a non-integral multiple of the desired drop flow rate.

27. Apparatus as set forth in claim 26, wherein said non-integral multiple varies over a range of approximately $2\frac{1}{2}$ to $15\frac{1}{2}$.

28. In a system for a parenteral administration of liquids by drop flow through a feeding tube, apparatus for controlling the rate of drop flow comprising:

tube clamping means normally maintaining said feeding tube in a substantially shut-off state;

driver means for selectively energizing said clamping means to unclamp said tube;

rate setting means for generating an electrical signal having a frequency greater than the desired drop flow rate, the ratio of said frequency to said desired drop flow rate being higher for relatively low drop flow rates than for relatively high drop flow rates;

flow monitoring means for monitoring actual drop flow through said feeding tube; and control means responsive to both said rate setting means and said flow monitoring means producing a train of control pulses at the frequency of said electrical signal for regulating the duration of each period of energization of said clamping means by said driver means.

29. In the parenteral administration of medical fluids by an intravenous set including drop forming means and fluid conduit means coupled to said drop forming means, a method of controlling the rate of drop flow through said fluid conduit means, comprising the steps of:

clamping said fluid conduit to a substantially shut-off state;

repetitively opening and closing said fluid conduit to fluid flow, the frequency of opening said fluid conduit being at a higher frequency than the desired drop flow rate through said fluid conduit, the ratio of said frequency of opening and closing to said desired drop flow rate being varied as a function of said desired drop flow rate.

30. In a system for parenteral administration of liquids by drop flow, apparatus for controlling the rate of drop flow comprising:

drop forming means;

a feeding tube coupled to said drop forming means;

tube clamping means for closing said feeding tube to prevent liquid flow therethrough;

flow rate setting means for designating a desired flow rate;

means responsive to said rate setting means for unclamping said tube at a selected frequency higher than the desired drop flow rate to allow repetitive liquid flow through said feeding tube, whereby a plurality of successive cycles of unclamping said tube are required to produce each individual drop of flow; and means for varying the ratio of said frequency of unclamping said tube to said desired drop flow rate as a function of said desired drop flow rate.

* * * * *

UNITED STATES PATENT AND TRADEMARK OFFICE
CERTIFICATE OF CORRECTION

PATENT NO. : 4,338,932

DATED : July 13, 1982

INVENTOR(S) : Heinz W. Georgi, Wallace L. Knute & Richard L. Foreman

It is certified that error appears in the above-identified patent and that said Letters Patent is hereby corrected as shown below:

Column 1, line 39, delete "nurse" and insert therefor --nurses--.

Column 4, line 28, after "drop", insert therein --flow--.

Column 9, line 4, delete "fo" and insert therefor --of--.

Signed and Sealed this

Seventh Day of February 1984

[SEAL]

Attest:

GERALD J. MOSSINGHOFF

Attesting Officer

Commissioner of Patents and Trademarks